(12) United States Patent
Qiu et al.

(10) Patent No.: US 6,403,849 B1
(45) Date of Patent: Jun. 11, 2002

(54) METHOD FOR PURIFYING PERFLUOROCARBONS

(75) Inventors: Zai-Ming Qiu; Zhongxing Zhang, both of Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/669,662

(22) Filed: Sep. 26, 2000

(51) Int. Cl.$^7$ ................................................. C07C 17/38
(52) U.S. Cl. ........................ 570/177; 570/178; 570/179; 570/180
(58) Field of Search ................................. 570/177, 131, 570/178, 179, 180

(56) References Cited

U.S. PATENT DOCUMENTS

| | | |
|---|---|---|
| 2,916,526 A | 12/1959 | Baranauckas et al. ...... 260/653 |
| 3,218,364 A | 11/1965 | Kometani et al. |
| 3,300,538 A | 1/1967 | Kometani et al. |
| 3,381,041 A | 4/1968 | Kometani et al. |
| 3,830,859 A | 8/1974 | Gordon et al. |
| 4,025,567 A | 5/1977 | Hutchinson et al. |
| 4,352,942 A | 10/1982 | Onopchenko et al. |
| 4,473,712 A | 9/1984 | Bonfield et al. |
| 4,814,518 A | 3/1989 | Gössel et al. |
| 4,849,557 A | 7/1989 | Kondo ........................ 570/177 |
| 4,929,753 A | 5/1990 | Gotoh et al. |
| 4,943,656 A | 7/1990 | Gallacher et al. |
| 5,387,323 A | 2/1995 | Minday et al. |
| 5,442,097 A | 8/1995 | Obermeier et al. |
| 5,684,210 A | 11/1997 | Kawai et al. |
| 5,744,661 A | 4/1998 | Luly et al. |

FOREIGN PATENT DOCUMENTS

| | | |
|---|---|---|
| FR | 90801 | 2/1968 |
| GB | 1362909 | 8/1974 |
| HU | 38117 | 4/1986 |
| JP | 58-144329 | 8/1983 |
| JP | 62-158238 | 7/1987 |
| JP | 4099737 | 3/1992 |
| JP | 6-228164 | 8/1994 |
| JP | 6-271487 | 9/1994 |
| JP | WO 98/26326 | 10/1995 |
| JP | WO 98/08789 | 3/1998 |
| SU | 1544788 | 2/1990 |

OTHER PUBLICATIONS

LaFave, *JACS*, 1949, 71:4148–4149.
Strachan et al., *ISEC '80*, 1980, "Aromatic Solubility in Aqueous Sulphuric Acid," pp. 1–6.
Zhu, *Synthesis*, 1993, "A Novel Reaction Medium: Perfluorocarbon Fluids," pp. 953–954.

*Primary Examiner*—Alan Siegel
(74) *Attorney, Agent, or Firm*—Lisa M. Fagan

(57) ABSTRACT

A method for obtaining purified perfluorocarbon compositions, and purified compositions containing such perfluorocarbons.

30 Claims, No Drawings

METHOD FOR PURIFYING PERFLUOROCARBONS

TECHNICAL FIELD

This invention relates to a method for obtaining purified perfluorocarbon compositions.

BACKGROUND

Perfluorocarbons such as perfluorooctane, known as fluorinerts, can be used as cleaning agents for electronics and other precision instruments. Perfluorocarbons can be prepared by electrochemical fluorination (ECF). Perfluorocarbons may be prepared with increased yields, greater efficiency and lower waste by electrochemically fluorinating trifluoromethyl-substituted aromatic compounds. For example, perfluorodimethylcyclohexane (PDMCH), which may be applicable to a wider range of uses than perfluorooctane by virtue of its lower pouring point, can be prepared by fluorinating its trifluoromethyl-containing aromatic counterpart, hexafluoroxylene (HFX), by the Simons process. The fluorination process results in a composition (or a mixture) containing primarily PDMCH and a small amount of HFX. Using physical methods such as fractional distillation to separate traces of HFX impurity from PDMCH is difficult, since HFX forms an azeotrope with PDMCH. Although prolonging the fluorination process may eventually reduce the amount of HFX in the PDMCH composition, this practice is not cost effective.

SUMMARY

Industrial cleaning applications require that a very low amount of HFX (less than about 100 ppm) be present in the final perfluorocarbon product, so there exists a need to obtain perfluorocarbon compositions with high purity. Due to the difficulties in obtaining high purity perfluorocarbon compositions, it is desirable to develop a method to conveniently and economically remove substantially all aromatic impurities from the perfluorocarbon composition.

In general, the invention relates to a method for obtaining a perfluorocarbon composition that is substantially free of aromatic impurities such as, for example, aromatic compounds containing a trifluoromethyl substituent. The method uses a chemical reaction to change the aromatic impurities, making them separable by physical methods by taking advantage of more advantageous solubility and/or boiling point, the absence of an azeotrope, and the like. The perfluorocarbon is substantially or completely unaffected by the chemical reaction and remains unchanged.

In one aspect, the invention features a method for obtaining a purified perfluorocarbon composition (i.e., a perfluorocarbon composition that is substantially free of aromatic impurities). The method includes providing a crude composition containing a perfluorocarbon and an aromatic impurity; and contacting the crude composition with a solubility-increasing reagent selected from the group consisting of concentrated sulfuric acid and oleum to convert the aromatic impurity into an aromatic compound having an acid functionality to form a first composition. Preferably, the aromatic compound having an acid functionality is removed from the first composition to form a purified perfluorocarbon composition.

In a second aspect, the invention also features a method for obtaining a perfluorocarbon composition that is substantially free of an aromatic impurity. The method includes providing a crude composition containing a perfluorocarbon and an aromatic impurity selected from the group consisting of 1,3-bis(trifluoromethyl)benzene, 1,4-bis(trifluoromethyl)benzene, trifluoromethylbenzene and mixtures thereof; contacting the crude composition with concentrated sulfuric acid or oleum at a temperature from about 100° C. to about 200° C.; and contacting the resulting composition with an alkaline aqueous solution to remove the aromatic impurities.

In a third aspect, the invention features a method for obtaining a perfluorocarbon composition that is substantially free of an aromatic impurity. The method includes fluorinating an aromatic compound to form a crude composition comprising a perfluorocarbon and an aromatic impurity; contacting the crude composition with a solubility-increasing reagent to convert the aromatic impurity into an aromatic compound having an acid functionality to form a first composition, wherein the solubility-increasing reagent is selected from the group consisting of sulfuric acid and oleum; and removing the aromatic compound having an acid functionality to form a purified composition comprising a perfluorocarbon.

In a fourth aspect, the invention features a method for purifying a perfluorocarbon composition. The method includes providing a crude composition containing a perfluorocarbon and an aromatic impurity; contacting the crude composition with a solubility-increasing reagent to form a first composition comprising a perfluorocarbon and an aromatic compound with an acid functionality; and removing the aromatic compound with an acid functionality to form a purified perfluorocarbon composition, wherein the aromatic compound and the aromatic impurity are present in the purified perfluorocarbon composition at a total concentration of less than about 100 ppm.

In a fifth aspect, the invention features a method for purifying a perfluorocarbon composition. The method includes providing a crude composition comprising a perfluorocarbon and an aromatic impurity, wherein the aromatic impurity has at least one unsubstituted ring carbon atom; contacting the crude composition with a solubility increasing reagent to form a first composition comprising a perfluorocarbon and an aromatic compound with an acid functionality; and contacting the first composition with an alkaline solution; and separating the alkaline solution to remove the aromatic compound with an acid functionality and form a second composition, wherein the second composition contains perfluorocarbons that are substantially free of aromatic impurities.

A purified perfluorocarbon composition prepared by each of the methods set forth above is also within the scope of this invention.

The invention also features a composition containing at least one of 1,3-perfluorodimethylcyclohexane and 1,4-perfluorodimethylcyclohexane, wherein the composition is substantially free of aromatic impurities. Such impurities are selected from the group consisting of 1,3-bis(trifluoromethyl)benzene, 1,4-bis(trifluoromethyl)benzene, and trifluoromethylbenzene and their total amount in the composition is no more than about 100 ppm; preferably, no more than 10 ppm; more preferably, no more than 1.0 ppm; most preferably no more than 0.1 ppm.

The details of one or more embodiments of the invention are set forth in the description below. Other features and advantages of the present invention will be apparent from the following description of the preferred embodiments, and also from the appending claims.

DETAILED DESCRIPTION

The invention relates to an efficient and economical method for obtaining a perfluorocarbon composition that is substantially free of an aromatic impurity, in particular, a trifluoromethyl-aromatic impurity. As used herein, a composition that is "substantially free" of a material means that the amount of the material is negligible in the composition, i.e., less than about 100 ppm. The purified perfluorocarbon compositions of the invention contain one or more perfluorocarbon compounds at a combined concentration of at least about 80 wt %, preferably at least about 99 wt %, and more preferably at least about 99.99 wt %, of the total weight of the composition. The purified fluorocarbon compositions of the invention also contain one or more aromatic impurities at a concentration of no more than about 100 ppm (based on the total weight of the composition).

The perfluorocarbons in the present composition are organic compounds in which all C—H bonds have been replaced by C—F bonds. In a preferred embodiment, the perfluorocarbon is selected from the group consisting of perfluoroalkanes (e.g., perfluorohexane, perfluoroheptane, or perfluorooctane), perfluorocycloalkanes (e.g., 1,3-perfluorodimethylcyclohexane, 1,4-perfluorodimethylcyclohexane, or perfluoromethylcyclohexane), and a mixture thereof. Preferably, the perfluorocarbon is 1,3-perfluorodimethylcyclohexane, 1,4-perfluorodimethylcyclohexane, perfluorooctane or a mixture thereof.

A preferred method for making these purified perfluorocarbon compositions includes: (1) providing a crude composition containing a perfluorocarbon and an aromatic impurity; and (2) contacting the crude composition with a solubility-increasing reagent selected from the group consisting of concentrated sulfuric acid and oleum to convert the aromatic impurity into an aromatic compound having an acid functionality to form a first composition. Preferably, the aromatic compound having an acid functionality is then removed from the first composition to form a purified perfluorocarbon composition.

As used herein, "solubility-increasing" means increasing solubility in polar solvents and water. However, increasing solubility in any solvent in which the perfluorocarbon is insoluble is also useful and within the scope of the present invention.

In the first step, the crude composition, which contains a mixture of perfluorocarbon and an aromatic impurity, may be prepared by any known process. For example, the crude composition can be obtained during the preparation of perfluorocarbon by an electrochemical fluorination (ECF) process. This process fluorinates a suitable organic compound, e.g., a trifluoromethyl-aromatic compound such as HFX, by the passage of a low potential electric current through an organic solution in anhydrous hydrogen fluoride in an electrochemical cell. A typical ECF process used to obtain a crude perfluorocarbon composition is described in U.S. Pat. No. 5,387,323.

As used herein, an aromatic impurity refers to an aromatic compound in the perfluorocarbon composition. Such an aromatic impurity, upon being treated with a solubility-increasing reagent under conditions as specified herein, is converted into an aromatic compound containing an acid functionality. The properties of the aromatic impurity and the acid functionalized aromatic compound are so different such that they can be separated from each other by physical methods. In a preferred embodiment, the aromatic impurity, which can be an aryl or a heteroaryl, has at least one (e.g., 1, 2, 3, or 4) unsubstituted ring carbon atom. As used herein, the term aryl refers to $C_{6-14}$ aromatic rings. These moieties may also be fused rings and can be fused with aryl or heteroaryl which is as defined below. Fused rings are rings that share a common carbon-carbon bond. Typically aryl groups include phenyl, naphthyl, indazolyl, phenanthryl, and anthracyl. The term heteroaryl means 6- to 14-membered aromatic rings that contain one or more heteroatoms selected from N, O, and S. These moieties may also be fused rings. Examples of heteroaryl groups include pyridyl, pyrazinyl, pyrimidyl, furyl, pyrrolyl, thienyl, thiazolyl, oxazolyl, imidazolyl, coumarinyl, indolyl, benzofuranyl, benzthiazolyl, benzothienyl, and benzothiadiazolyl.

The aromatic impurity is optionally substituted with a substituent selected from the group consisting of alkyl, cycloalkyl, heterocycloalkyl, aryl, heteroaryl, aralkyl, heteroaralkyl, halo, and haloalkyl. Alkyl substituents include straight chains that contain 1–10 carbon atoms, or a branched hydrocarbon chain of 3–10 carbon atoms, or cyclic hydrocarbon groups containing 3–10 carbon atoms. The cyclic alkyl groups may contain one or more heteroatoms, which are, typically, nitrogen, oxygen, or sulfur. Examples of alkyl groups include, but are not limited to, methyl, ethyl, propyl, isopropyl, butyl, isobutyl, tert-butyl, amyl, pentyl, hexyl, heptyl, octyl, cyclopropyl, cyclopentyl, cyclohexyl, cycloheptyl, piperidinyl, morpholino and pyrrolindinyl groups. As used herein, the term "halo" refers to fluoro, chloro, bromo, or iodo.

Preferably, the aromatic impurity is an aryl compound substituted with at least one of alkyl and haloalkyl (e.g., trifluoromethyl). Examples of the aromatic impurity include benzene, naphthalene, anthracene, phenanthrene, fluorene, pyrrole, indole, quinoline, furan, benzofuran, and halo-substituted, alkyl-substituted, or haloalkyl-substituted derivatives thereof. Some particular preferred examples of an aromatic impurity are 1,3-bis(trifluoromethyl)benzene, 1,4-bis(trifluoromethyl)benzene, and trifluoromethylbenzene.

However, aromatic impurities that do not contain a trifluoromethyl group can also be removed from the perfluorocarbon composition. Rather than hydrolysis, which takes place at the trifluoromethyl substituent, these aromatic impurities (containing at least one unsubstituted ring carbon atom) would undergo sulfonation when treated with concentrated sulfuric acid or oleum, which would form a sulfonate substituent —$SO_3H$. Similar to aromatic compounds containing a carboxyl group, those containing such a sulfonate substituent also possesses substantially different properties than the perfluorocarbons, e.g., having a higher water solubility. Therefore, these aromatic compounds can also be separated from the perfluorocarbons by physical methods.

It should be noted that nitrogen-containing aromatic impurities when treated with concentrated sulfuric acid or oleum may form salts and/or undergo oxidative ring opening. Such reaction products are also expected to be more effectively separable from the perfluorocarbons by physical methods than their unreacted precursors.

In the second step of the preferred method, a solubility-increasing reagent is used to convert the aromatic impurity in the crude composition into its derivatives that contain an acid functionality. Solubility-increasing reagents include compounds that react with an aromatic impurity to form an aromatic compound with an acid functionality. Some typical examples of solubility increasing reagents are concentrated sulfuric acid and oleum. Suitable solubility increasing reagents include concentrated sulfuric acid (95–98% w/v), oleum (concentrated sulfuric acid containing 10–40 wt % $SO_3$, preferably, 20–30 wt % $SO_3$). Preferably, the solubility-increasing reagent is concentrated sulfuric acid or oleum; more preferably, oleum (1–3 wt % of the crude composition). For oleum, the $SO_3$ content is closely related to its reactivity. Higher fuming ($SO_3$) content results in higher reaction rate. Note that two or more solubility-increasing reagents can be employed simultaneously. If concentrated sulfuric acid and/or oleum is used, care should be taken to eliminate as much water in the reaction mixture as possible since water will reduce the sulfuric acid concentration or reduce the fuming content of oleum. Further, the reactor containing concentrated sulfuric acid and/or oleum should be filled with more than 50% of the reaction mixture to minimize the waste of the sulfuric acid and/or oleum caused by escaping fuming gas in the vapor space.

The solubility-increasing reagent converts the aromatic impurity in the crude composition into its derivatives that contain an acid functionality. As used herein, an acid functionality is a chemical group that acts as a proton donor in a neutral aqueous solution (i.e., at about pH 7.0), thus forming a charged group. In other words, an acid functionality has a $pK_a$ of higher than 7.0. Generally, such acid functionality-containing compounds have higher solubility in aqueous solutions than their pre-treated aromatic counterparts. Furthermore, said acid functionality-containing compounds have significantly different boiling points than their aromatic impurity precursors. As such, the acid functionality-containing compounds can be more readily separated from the perfluorocarbons than their aromatic impurity precursors by other physical methods, including but not limited to distillation. The acid functionality thus formed is preferably selected from the group consisting of carboxyl and sulfonic acid; more preferably, the acid functionality is carboxyl.

For example, the trifluoromethyl groups in HFX are converted into carboxyl groups after being treated with a solubility-increasing reagent such as oleum. These trifluoromethyl-containing aromatic compounds are relatively inert, but under suitable conditions, the trifluoromethyl group can undergo hydrolysis to form a carboxyl group, giving rise to hydrogen fluoride as a by-product. The perfluorocarbons in the composition are not affected (due to their inertness) by the treatment with a solubility-increasing reagent.

Typically, the ratio of the amount of perfluorocarbon to the amount of the solubility-increasing reagent (by weight) can range from about 5:1 to about 400:1; preferably, from about 10:1 to about 300:1; more preferably, from about 20:1 to about 200:1. Note that the perfluorocarbon compound can function as a solvent. Since the amount of aromatic impurity is usually low in a crude composition, excess solubility-increasing reagent should be employed for the reaction to complete in a reasonable time period. In general, the ratio of the amount of the aromatic impurity to the amount of the solubility-increasing reagent (by weight) can range from about 1:1 to about 1:2000, preferably, from about 1:1 to about 1:1000, more preferably, from about 1:1 to about 1:200.

The temperature at which the reaction should take place can range from room temperature to about 200° C.; preferably, from about 100° C. to about 180° C.; more preferably, from about 120° C. to about 160° C. For example, it has been found that the reaction between oleum (i.e., about 20–30% fuming sulfuric acid) present at about 1 wt % to 3 wt % and 1,3-HFX or 1,4-HFX (present at less than about 1 wt %) at about 150° C. proceeds rapidly, e.g., in less than about two hours. The reaction can also take place in a dry, inert atmosphere, e.g., in nitrogen or argon.

The products (i.e., the acid functionality-containing aromatic compounds) formed in the first two steps discussed above possess substantially different properties than their pre-treated counterparts, as well as the perfluorocarbons that remain in the resulting composition. The optional last step of the preferred method takes advantage of this feature and separates the aromatic compounds from the perfluorocarbon compounds by physical means. For example, the aromatic compounds possess a different boiling point than the perfluorocarbons, and can be separated by distillation. As another example, the aromatic compounds have a higher solubility in aqueous solution than the perfluorocarbons and can be removed by contacting (or washing) the composition with an aqueous solution. Preferably, the aqueous solution is alkaline (e.g., about 1 to about 10 wt % NaOH solution such as about 5% NaOH solution). Note that any alkaline aqueous solution can be employed. The aqueous solution, when added to the perfluorocarbon composition, forms two separate layers, an organic layer and an aqueous layer. Due to the difference in solubility between the aromatic compound containing an acid functionality and the perfluorocarbon compound, the former tends to stay in the aqueous layer whereas the latter tends to stay in the organic layer. Separation of the two layers thereby removes the aromatic compound containing an acid functionality from the perfluorocarbon compound, thus resulting in a purified perfluorocarbon composition.

The purified perfluorocarbon compositions thus formed contain one or more perfluorocarbon compounds at a combined concentration of at least about 80 wt %, preferably at least about 99 wt %, and more preferably at least about 99.99 wt %, of the total weight of the composition. The purified perfluorocarbon compositions contain no more than about 100 ppm of an aromatic impurity (including its acidic functionality-containing derivatives); preferably, no more than about 10 ppm; more preferably, no more than about 1.0 ppm; most preferably no more than about 0.1 ppm. Without further elaboration, it is believed that one skilled in the art can, based on the description herein, utilize the present invention to its fullest extent. The following specific examples are, therefore, to be construed as merely illustrative, and not limitative of the remainder of the disclosure in any way whatsoever. All patents and publications recited herein are incorporated by reference in their entirety.

EXAMPLES

Preparation Example
Preparation of PDMCH Cell Crude by the Electrochemical Fluorination (ECF) of Hexafluoroxylene A 2.5 liter Simons electrochemical fluorination cell was equipped with a pair of nickel electrodes (area 370 cm$^2$) and two overhead condensers having brine temperatures of 18° C. and −40° C. respectively. The cell was charged with 1.7 kg of anhydrous hydrogen fluoride and 12 grams of dimethyl disulfide (DMDS). After being heated to 50° C., the electrochemical fluorination was started by applying a direct current (DC) at a voltage of 5.5 volts and allowing the DC to vary. The ECF system pressure was controlled at 2311 torr (30 psig). Five hours after the voltage was applied, a feed of 1,4-bis(trifluoromethyl)benzene (hexafluoroxylene) containing 5 weight % DMDS was started at 8.5 grams per hour and the current was maintained at 30 amps. After 48 hours, the feed of hexafluoroxylene was stopped but the ECF was continued. The voltage was gradually increased in order to keep the electric current above 2 amps. When the voltage was raised to 8 volts but the current was below 2 amps, the ECF process was stopped by turning off the DC power. The ECF crude was drawn from the bottom of the cell through a drain valve.

Example 1
Removal of 1,4-HFX from PDMCH with Oleum in Tube Reactor

In a 120 ml tube reactor equipped with a magnetic stir bar were charged 0.3 g oleum (fuming sulfuric acid containing 30 weight % $SO_3$) and 30 g 1,4-perfluorodimethyl-cyclohexane (PDMCH) containing 400 ppm 1,4-bis (trifluoromethyl)benzene (1,4-HFX) under a nitrogen atmosphere. The tube was sealed and immersed in a 150° C. oil bath. The mixture was stirred with refluxing inside the tube for 2 hours. The reactor tube was then cooled, and the mixture was washed with 10 ml of 5% aqueous sodium hydroxide, followed by two 10 ml water washings. Upon gas chromatographic (GC) analysis of the resulting isolated PDMCH, no detectable amount of 1,4-HFX was found. The detection limit for 1,4-HFX was about 1 ppm.

Example 2
Removal of 1,4-HFX from PDMCH with Oleum in Parr Reactor

In a 600 ml Parr reactor were charged 14 g oleum (20 weight % $SO_3$) and 400 g PDMCH containing 700 ppm 1,4-HFX under a nitrogen atmosphere. The reactor was sealed and heated to 150° C. After reacting for 2 hours at 150° C., the reaction mixture was stopped by cooling the reactor to 0° C. The mixture was then washed as described in Example 1. The resulting isolated PDMCH was subjected to GC analysis. No detectable amount of 1,4-HFX was found.

Example 3
Removal of 1,4-HFX from PDMCH with Concentrated Sulfuric Acid

In a 25 ml tube reactor were charged 1 g concentrated sulfuric acid, 1 g PDMCH, and 1 g 1,4-HFX. The reactor was sealed and heated to 100° C. in an oil bath for 4 hours before the reaction was stopped by cooling the reactor to room temperature. The resulting reaction mixture was combined with 10 ml of water, resulting in the formation of a solid precipitate. The precipitate was then dissolved in 5% aqueous sodium hydroxide. The PDMCH layer was separated from the water layer and was analyzed by GC for 1,4-HFX content, which was found to be 15.5 weight %. This corresponded to a removal of 69 weight % of the 1,4-HFX, which was originally present at a level of 50 weight %. The aqueous solution was acidified, thereby re-forming a solid precipitate. NMR analysis of the solid precipitate revealed its identity as terephthalic acid ($^1$H NMR: 11.7 (2H) ppm, 8.02 (4H) ppm, $^{13}$C NMR: 166.8 ppm, 134.6 ppm, 129.6 ppm) and a small amount of 4-trifluoromethylbenzoic acid ($^{19}$F NMR: 61.2 ppm).

Example 4
Removal of 1,3-HFX from PDMCH with Oleum

PDMCH (30 g) containing 2 weight % 1,3-bis (trifluoromethyl)benzene (1,3-HFX) was treated with oleum (1.0 g) essentially as described in Example 1. After the reaction had proceeded for 0.5 hour at 140° C., GC analysis of a small quantity of the reaction mixture (twice washed with water) indicated that 97 weight % of the 1,3-HFX was removed. After a total of 1 hour of reaction at 140° C., the presence of 1,3-HFX was undetectable by GC analysis. The reaction mixture was transferred to a beaker containing 30 ml water, resulting in the formation of a solid precipitate. The precipitate was collected by filtration and found to be soluble in 5% aqueous sodium hydroxide. FT-IR analysis of the precipitate revealed a strong signal at 1687 $cm^{-1}$, indicating the formation of carboxylic acid(s). NMR analysis of the precipitate indicated mainly the presence of isophthalic acid ($^1$H NMR: 13.2 (2H) ppm, 8.47 (t, 1H) ppm, 4.14 (dxm, 2H) ppm, 7.60 (t, 1H) ppm; $^{13}$C NMR: 166.8 ppm, 133.5 ppm, 131.3 ppm, 129.2 ppm) and a small amount of m-trifluoromethylbenzoic acid ($^{19}$F NMR: 6.10 ppm). The PDMCH was recovered by separation from the water layer using a separatory funnel.

Example 5
Removal of 1,3-HFX from PDMCH with Concentrated Sulfuric Acid

Using the procedure of Example 3, PDMCH (10 g) containing 2 weight % 1,3-HFX was treated with concentrated sulfuric acid (95–98 weight %) (1.0 g). After reacting for 3 hours at 145° C., the reaction mixture was analyzed by GC, which indicated the presence of 0.74 weight % 1,3-HFX. The reaction was continued for 8 additional hours, and the weight % of 1,3-HFX in the resulting reaction mixture was found by GC analysis to be 0.06 weight %.

Example 6
Removal of Trifluoromethylbenzene from PDMCH with Concentrated Sulfuric Acid Using the procedure essentially as described in Example 3, PDMCH (10 g) containing 2 weight % trifluoromethylbenzene (TFT) was treated with concentrated sulfuric acid (95–98 weight %) (2.0 g). After reacting for 1 hour at 145° C., the reaction mixture contained 0.072 weight % TFT as determined by GC analysis. The reaction was continued for 2 additional hours, and no TFT was found by GC analysis in the resulting reaction mixture after aqueous base wash. (The detection limit for TFT was about 1 ppm.) The reaction mixture was then cooled to room temperature and poured into a beaker containing 10 ml of water. A white solid precipitated formed and was isolated by filtration. FT-IR analysis of the solid showed a strong signal at 1687 $cm^{-1}$. The melting point of the solid was found to be 119–123° C. These findings indicated that the solid was benzoic acid.

Example 7
Removal of Trifluoromethylbenzene from Perfluorooctane with Oleum

In a 25 ml reactor tube were charged 20 g of perfluorooctane (FC5080, available from 3M Performance Materials, St. Paul, Minn.) and 0.5 g of TFT. A GC chromatogram obtained by analyzing the resulting solution indicated two peaks with area ratios of 92.21% to 7.29%. They corresponded to perfluorooctane and TFT, respectively. Oleum (0.5 g) was added to the solution, and after sealing the tube the mixture was reacted at room temperature overnight. A dark top layer was separated. A small portion of the bottom layer was taken and after water washing was found by GC analysis to produce a peak area ratio of 99.73% to 0.27%. The reaction was allowed to continue for 2 additional hours at 150° C. GC analysis showed no detectable amount of TFT present.

Example 8
Removal of Toluene from Perfluorooctane with Oleum

In a 25 ml reactor tube were charged with perfluorooctane (20 g) and toluene (0.5 g). A two layer mixture formed, and GC analysis of the bottom perfluorooctane layer produced a chromatogram with peak area ratios of 94.5% to 5.5%, which corresponded to perfluorooctane and toluene, respectively. Oleum (1 g) was added to the mixture, and after sealing the tube the mixture was allowed to react at 150° C. for 2 hours. A small portion of the bottom layer was then taken and washed with aqueous base. GC analysis of the resulting isolated organic layer showed two signals in a ratio of 99.81% to 0.19%. The reaction continued for 2 additional hours at 150° C. GC analysis of a small, aqueous base washed portion of the resulting reaction mixture showed no detectable amount of toluene present. The detection limit for toluene was about 1 ppm.

Example 9
Removal of N-Methylpyrrole from Perfluorooctane with Oleum

In a 60 ml Ace heavy-wall pressure tube perfluorooctane (20 g) and N-methylpyrrole (0.5 g) were mixed (forming two layers). GC analysis of a small sample of the bottom, perfluorooctane layer showed a peak area ratio of 98.72% to 1.28%, corresponding to perfluorooctane and N-methylpyrrole, respectively. Oleum (1.0 g) was added to the mixture. After sealing the reactor tube, which contained the mixture, it was heated at 100° C. for four hours. The resulting mixture was then transferred into 10 ml ice-water and washed twice with water. The isolated perfluorooctane layer was analyzed by GC, and no N-methylpyrrole was detected. The detection limit for N-methylpyrrole was about 1 ppm.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for obtaining a perfluorocarbon composition that is substantially free of an aromatic impurity, the method comprising:
   (a) providing a crude composition comprising a perfluorocarbon and one or more aromatic impurity where at least one aromatic impurity is substituted with a trifluoromethyl group;
   (b) contacting the crude composition with a solubility-increasing reagent selected from the group consisting of concentrated sulfuric acid and oleum to convert the aromatic impurity into an aromatic compound having an acid functionality to form a first composition; and
   (c) removing the aromatic compound having an acid functionality from the first composition to form a purified perfluorocarbon composition.

2. The method of claim 1, wherein the one or more aromatic impurity has at least one unsubstituted ring carbon atom.

3. The method of claim 1, wherein the aromatic compound is removed by contacting the first composition with an alkaline solution.

4. The method of claim 3 further comprising separating the alkaline solution from the purified perfluorocarbon composition.

5. The method of claim 1, wherein the perfluorocarbon is selected from the group consisting of perfluoroalkanes and perfluorocycloalkanes.

6. The method of claim 1, wherein the perfluorocarbon is selected from the group consisting of 1,3-perfluorodimethylcyclohexane, 1,4-perfluorodimethylcyclohexane, perfluoromethylcyclohexane, perfluorohexane, perfluoroheptane, perfluorooctane and mixtures thereof.

7. The method of claim 1, wherein the perfluorocarbon is selected from the group consisting of 1,3-perfluorodimethylcyclohexane, 1,4-perfluorodimethylcyclohexane, perfluorooctane and mixtures thereof.

8. The method of claim 1, wherein the one or more aromatic impurity is an aryl compound substituted with at least one of alkyl and haloalkyl.

9. The method of claim 8, wherein either of the aryl and the heteroaryl compounds are substituted with a substituent selected from the group consisting of alkyl, cycloalkyl, heterocycloalkyl, aryl, heteroaryl, aralkyl, heteroaralkyl, halo, and haloalkyl.

10. The method of claim 9, wherein the one or more aromatic impurity is an aryl compound substituted with at least one of alkyl and haloalkyl.

11. The method of claim 10, wherein the one or more aromatic impurity is selected from the group consisting of 1,3-bis(trifluoromethyl)benzene, 1,4-bis(trifluoromethyl)benzene, and trifluoromethylbenzene.

12. The method of claim 1, wherein the acid functionality is selected from the group consisting of carboxylic acid and sulfonic acid.

13. The method of claim 1, wherein the acid functionality is a carboxylic acid.

14. The method of claim 1, wherein the solubility-increasing reagent is oleum.

15. The method of claim 1, wherein the ratio by weight of the amount of perfluorocarbon to the amount of the solubility-increasing reagent ranges from about 20:1 to about 200:1.

16. The method of claim 1, wherein the ratio by weight of the amount of the one or more aromatic impurity to the amount of the sdlubility-increasing reagent ranges from about 1:1 to about 1:2000.

17. The method of claim 1, wherein the ratio by weight of the amount of the one or more aromatic impurity to the amount of the solubility-increasing reagent ranges from about 1:1 to about 1:1000.

18. The method of claim 1, wherein the ratio by weight of the amount of the one or more aromatic impurity to the amount of the solubility-increasing reagent ranges from about 1:1 to about 1:200.

19. The method of claim 1, wherein the crude composition is contacted with the solubility-increasing reagent at a temperature ranging from room temperature to about 200° C.

20. The method of claim 19, wherein the temperature ranges from about 100° C. to about 180° C.

21. The method of claim 1, wherein the purified perfluorocarbon composition comprises no more than about 100 ppm of an aromatic impurity.

22. The method of claim 1, wherein the purified perfluorocarbon composition comprises no more than about 10 ppm of an aromatic impurity.

23. The method of claim 1, wherein the purified perfluorocarbon composition comprises no more than about 0.1 ppm of an aromatic impurity.

24. A method for obtaining a perfluorocarbon composition that is substantially free of an aromatic impurity, the method comprising:
   (a) providing a crude composition comprising a perfluorocarbon and an aromatic impurity selected from the group consisting of 1,3-bis(trifluoromethyl)benzene, 1,4-bis(trifluoromethyl)benzene, trifluoromethylbenzene and mixtures thereof;

(b) contacting the crude composition with concentrated sulfuric acid or oleum at a temperature from about 100° C. to about 200° C.; and (c) contacting the resulting composition with an alkaline aqueous solution to remove the aromatic impurities.

25. A method for obtaining a perfluorocarbon composition that is substantially free of an aromatic impurity, the method comprising:

(a) fluorinating an aromatic compound to form a crude composition comprising a perfluorocarbon and an aromatic impurity;

(b) contacting the crude composition with a solubility-increasing reagent to convert the aromatic impurity into an aromatic compound having an acid functionality to form a first composition, wherein the solubility-increasing reagent is selected from the group consisting of sulfuric acid and oleum; and (c) removing the aromatic compound having an acid functionality to form a purified composition comprising a perfluorocarbon.

26. The method of claim 25, wherein the aromatic compound is removed by contacting the first composition with an alkaline aqueous solution.

27. The method of claim 25, wherein the aromatic compound and the aromatic impurity are present in the purified perfluorocarbon composition at a total concentration of less than about 100 ppm.

28. A method for purifying a perfluorocarbon composition, comprising:

(a) providing a crude composition comprising a perfluorocarbon and an aromatic impurity;

(b) contacting the crude composition with a solubility increasing reagent selected from the group consisting of concentrated sulfuric acid and oleum to form a first composition comprising a perfluorocarbon and an aromatic compound with an acid functionality; and (c) removing the aromatic compound with an acid functionality to form a purified perfluorocarbon composition, wherein the aromatic compound and the aromatic impurity are present in the purified perfluorocarbon composition at a total concentration of less than about 100 ppm.

29. The method of claim 28, wherein the aromatic compound is removed by contacting the first composition with an alkaline solution.

30. A method for purifying a perfluorocarbon composition, comprising:

(a) providing a crude composition comprising a perfluorocarbon and an aromatic impurity, wherein the aromatic impurity has at least one unsubstituted ring carbon atom;

(b) contacting the crude composition with a solubility increasing reagent selected from the group consisting of concentrated sulfuric acid and oleum to form a first composition comprising a perfluorocarbon and an aromatic compound with an acid functionality;

(c) contacting the first composition with an alkaline solution; and (d) separating the alkaline solution to remove the aromatic compound with an acid functionality to form a second composition, wherein the second composition comprises perfluorocarbons that are substantially free of aromatic impurities.

* * * * *

UNITED STATES PATENT AND TRADEMARK OFFICE
CERTIFICATE OF CORRECTION

PATENT NO.     : 6,403,849 B1
DATED          : June 11, 2002
INVENTOR(S)    : Qiu, Zai-Ming It is certified that error appears in the above-identified patent and that said Letters Patent is hereby corrected as shown below:

<u>Column 10,</u>
Line 37, "sdlubility-increasing" should read -- solubility-increasing --.

Signed and Sealed this

Twenty-eighth Day of January, 2003

JAMES E. ROGAN
*Director of the United States Patent and Trademark Office*